United States Patent [19]

Rivier et al.

[11] Patent Number: 4,489,163

[45] Date of Patent: Dec. 18, 1984

[54] RCRF AND ANALOGS

[75] Inventors: Jean E. F. Rivier, La Jolla; Joachim Spiess, Encinitas; Wylie W. Vale, Jr., La Jolla, all of Calif.

[73] Assignee: The Salk Institute for Biological Studies, San Diego, Calif.

[21] Appl. No.: 484,931

[22] Filed: Apr. 14, 1983

[51] Int. Cl.³ .................. G01N 1/00; A61K 37/00; C07C 103/52
[52] U.S. Cl. ..................... 436/86; 424/2; 424/177; 260/112.5 R
[58] Field of Search .................. 424/177, 2; 260/112.5 R; 436/86

[56] References Cited

PUBLICATIONS

Bristow, et al., J. of Endocrinology (1980), 84, 189–197.
Science, Sep. 18, 1981, Vale et al., pp. 1394–1394, "Characterization of a 41-Residue Ovine Hypothalamic Peptide that Stimulates Secretion of Corticotropin and β-Endorphin".
Peptides, vol. 3, pp. 859–867 (1982), Ichikawa, et al., "Isolation and Amino Acid Sequence of Urotensin I, a Vasoactive and ACTH–Releasing Neuropeptide, from the Carp (Cyprinus Carpio) Urophysis".

*Primary Examiner*—Delbert R. Phillips

*Attorney, Agent, or Firm*—Fitch, Even, Tabin & Flannery

[57] ABSTRACT rCRF (rat Corticotropin Releasing Factor) has been isolated, characterized and found to have the formula: H-Ser-Glu-Glu-Pro-Pro-Ile-Ser-Leu-Asp-Leu-Thr-Phe-His-Leu-Leu-Arg-Glu-Val-Leu-Glu-Met-Ala-Arg-Ala-Glu-Gln-Leu-Ala-Gln-Gln-Ala-His-Ser-Asn-Arg-Lys-Leu-Met-Glu-Ile-Ile-NH$_2$. Analogs are disclosed that are at least as potent as rCRF, and rCRF or these analogs orpharmaceutically or veterinarily acceptable salts thereof, dispersed in a pharmaceutically or veterinarily acceptable liquid or solid carrier, can be administered to animals, including humans, to achieve a substantial elevation of ACTH, β-endorphin, β-lipotropin, other products of the pro-opiomelanocortin gene and corticosterone levels and/or a lowering of blood pressure over an extended period of time. They may also be used as stimulants to elevate mood and improve memory and learning, as well as diagnostically.

In the analogs, one or more of the first three N-terminal residues may be deleted or may be substituted by a peptide up to 10 amino acids long and/or by an acylating agent containing up to 7 carbon atoms. A number of other substitutions may also be made throughout the chain.

20 Claims, No Drawings

RCRF AND ANALOGS

This invention was made with Government support under Grant No. Am-26741 awarded by the National Institutes of Health. The Government has certain rights in this invention.

This invention is directed to peptides and to methods for pharmaceutical treatment of animals using such peptides. More specifically, the invention relates to the hentetracontapeptide rCRF, to analogs of rCRF, to pharmaceutical compositions containing rCRF or such analogs and to methods of treatment of animals using rCRF or such analogs.

BACKGROUND OF THE INVENTION

Experimental and clinical observations have supported the concept that the hypothalamus plays a key role in the regulation of adenohypophysial corticotropic cells secretory functions. Over 25 years ago, Guillemin, Rosenberg and Saffran and Schally independently demonstrated the presence of factors in hypothalamus which would increase the rate of ACTH secretion by the pituitary gland incubated in vitro or maintained in an organ culture. None of the secretagogs characterized mets the criteria expected of a physiologic corticotropin releasing factor (CRF) until ovine CRF (oCRF) was characterized in 1981 and was found to have the formula:

H-Ser-Gln-Glu-Pro-Pro-Ile-Ser-Leu-Asp-Leu-Thr-Phe-His-Leu-Leu-Arg-Glu-Val-Leu-Glu-Met-Thr-Lys-Ala-Asp-Gln-Leu-Ala-Gln-Gln-Ala-His-Ser-Asn-Arg-Lys-Leu-Leu-Asp-Ile-Ala-NH$_2$.

Sauvagine is a 40-residue, amidated generally similar peptide which was isolated from the skin of the South American frog Phyllomedusa sauvagei. It was characterized by Erspamer et al. and was described in *Regulatory Peptides*, Vol. 2 (1981), pp. 1–13. Sauvagine has the formula: pGlu-Gly-Pro-Pro-Ile-Ser-Asp-Leu-Ser-Leu-Glu-Leu-Leu-Arg-Lys-Met-Ile-Glu-Ile-Glu-Lys-Gln-Glu-Lys-Glu-Lys-Gln-Gln-Ala-Ala-Asn-Asn-Arg-Leu-Leu-Leu-Asp-Thr-Ile-NH$_2$. Sauvagine and oCRF have been reported to have biological activity in lowering blood pressure in mammals and in stimulating the secretion of ACTH and β-endorphin. The purification of another CRF has been pursued, using as a starting material 100,000 lyophilized rat hypothalami.

SUMMARY OF THE INVENTION

Rat CRF (rCRF) has now been isolated, purified and characterized as a hentetracontapeptide having the formula: H-Ser-Glu-Glu-Pro-Pro-Ile-Ser-Leu-Asp-Leu-Thr-Phe-His-Leu-Leu-Arg-Glu-Val-Leu-Glu-Met-Ala-Arg-Ala-Glu-Gln-Leu-Ala-Gln-Gln-Ala-His-Ser-Asn-Arg-Lys-Leu-Met-Glu-Ile-Ile-NH$_2$. It may alternatively be referred to as rat Amunine. The synthesis of the 41-residue peptide has been completed, and both the isolated rCRF and the synthetic rCRF stimulate ACTH and β-endorphin activies in vitro and in vivo. Synthetic rCRF has been found to substantially lower blood pressure for an extended time period. As a result synthetic rCRF is available in substantially pure form (i.e. substantially free of the remainder of a crude biological extract or of related synthetic replicates), and synthetic compounds having a purity of at least about 5%, which is substantially higher in purity than the naturally occurring peptide, are considered to have utility. A purity of at least about 90% or higher is practically obtainable and would likely be used for clinical testing.

Analogs of the 41-residue peptide rCRF having the following formula have at least substantially the same biological activity:

Y-$R_1$-Pro-Pro-Ile-Ser-$R_8$-Asp-Leu-$R_{11}$-$R_{12}$-$R_{13}$-Leu-Leu-Arg-$R_{17}$-$R_{18}$-$R_{19}$-Glu-$R_{21}$-$R_{22}$-$R_{23}$-$R_{24}$-$R_{25}$-$R_{26}$-$R_{27}$-$R_{28}$-Gln-Gln-Ala-$R_{32}$-$R_{33}$-Asn-Arg-$R_{36}$-Leu-$R_{38}$-$R_{39}$-$R_{40}$-$R_{41}$-NH$_2$ wherein Y is hydrogen or an acyl group having 7 or less carbon atoms and/or a peptide up to 10 residues long; $R_1$ is Ser-Gln-Glu or pGlu-Gly or Gln-Glu or Glu or D-Ser-Gln-Glu or Ser-Glu-Glu or D-Ser-Glu-Glu or Glu-Glu or D-pGlu-Gly or des$R_1$; $R_8$, $R_{12}$, $R_{19}$, $R_{24}$ and $R_{40}$ are selected from the group consisting of Leu, Ile, Ala, Gly, Val, Nle, Phe and Gln; $R_{11}$ is Thr or Ser; $R_{13}$ is His, Tyr or Glu; $R_{17}$ is Glu or Lys; $R_{18}$ is Val or Met; $R_{21}$ is Met, Met(O), Ile, Ala, Leu, Gly, Nle, Val, Phe or Gln; $R_{22}$ is Ala or Thr or Glu; $R_{23}$ is Arg or Lys; $R_{25}$ is Asp or Glu; $R_{26}$ is Gln or Lys; $R_{27}$ is Leu, Ile, Ala, Gly, Val, Nle, Phe, Asp, Asn, Gln or Glu; $R_{28}$ is Ala or Lys; $R_{32}$ is His, Tyr or Ala; $R_{33}$ is Ser, Asn, Leu, Thr or Ala; $R_{36}$ is Lys or Leu; $R_{38}$ is Met or Leu; $R_{39}$ is Glu or Asp; $R_{41}$ is Ala, Ile, Gly, Val, Leu, Nle, Phe, Gln or des $R_{41}$, provided however that when $R_{38}$ is Leu, then $R_{22}$ is Ala.

Pharmaceutical compositions in accordance with the invention include rCRF or its analogs, or nontoxic addition salts thereof, dispersed in a pharmaceutically or veterinarily acceptable liquid or solid carrier. The administration of such peptides or pharmaceutically or veterinarily acceptable addition salts thereof to animals, particularly mammals, in accordance with the invention may be carried out for the regulation of secretion of ACTH, β-endorphin, β-lipotropin, other products of the pro-opiomelanocortin gene and corticosterone and/or for the lowering of blood pressure and/or for affecting mood, behavioral and gastrointestinal functions and automatic nervous system activities. Furthermore rCRF and its analogs may be used for the evaluation of the status of pituitary, cardiovascular, gastrointestinal or central nervous system functions.

DETAILED DESCRIPTION OF THE PREFERRED EMBODIMENTS rCRF has been isolated from rat hypothalamic extracts, purified and characterized. The nomenclature used to define the peptides is that specified by Schroder & Lubke, "The Peptides", Academic Press (1965) wherein, in accordance with conventional representation, the amino group appears to the left and the carboxyl group to the right. Where the amino acid residue has isomeric forms, it is the L-form of the amino acid that is represented unless otherwise expressly indicated.

The invention provides rCRF and analogs of rCRF having the following formula:

Y-$R_1$-Pro-Pro-Ile-Ser-$R_8$-Asp-Leu-$R_{11}$-$R_{12}$-$R_{13}$-Leu-Leu-Arg-$R_{17}$-$R_{18}$-$R_{19}$-Glu-$R_{21}$-$R_{22}$-$R_{23}$-$R_{24}$-$R_{25}$-$R_{26}$-$R_{27}$-$R_{28}$-Gln-Gln-Ala-$R_{32}$-$R_{33}$-Asn-Arg-$R_{36}$-Leu-$R_{38}$-$R_{39}$-$R_{40}$-$R_{41}$-NH$_2$ wherein Y is hydrogen or an acyl group having 7 or less carbon atoms and/or a peptide up to 10 residues long; $R_1$ is Ser-Gln-Glu or pGlu-Gly or Gln-Glu or Glu or D-Ser-Gln-Glu or Ser-Glu-Glu or D-Ser-Glu-Glu or Glu-Glu or D-pGlu-Gly or des$R_1$; $R_8$, $R_{12}$, $R_{19}$, $R_{24}$ and $R_{40}$ are selected from the group consisting of Leu, Ile, Ala, Gly, Val, Nle, Phe and Gln; $R_{11}$ is Thr or Ser; $R_{13}$ is His, Tyr or Glu; $R_{17}$ is Glu or Lys; $R_{18}$ is Val or Met; $R_{21}$ is Met, Met(O), Ile, Ala, Leu, Gly, Nle, Val, Phe or Gln; $R_{22}$ is Ala, Thr or Glu; $R_{23}$ is Arg or Lys; $R_{25}$ is Asp or Glu; $R_{26}$ is Gln or Lys; $R_{27}$ is Leu, Ile, Ala, Gly, Val, Nle, Phe, Asp, Asn, Gln or Glu; $R_{28}$ is Ala or Lys; $R_{32}$ is His, Tyr or Ala; $R_{33}$ is Ser, Asn, Leu, Thr or Ala; $R_{36}$ is Lys or Leu; $R_{38}$ is Met or Leu; $R_{39}$ is Glu or Asp; $R_{41}$ is Ala, Ile, Gly, Val, Leu, Nle, Phe, Gln or des $R_{41}$, provided however that when $R_{38}$ is Leu, then $R_{22}$ is Ala. In a preferred group of rCRF analogs, $R_{13}$ is His $R_{17}$ is Glu, $R_{18}$ is Val, $R_{26}$ is Gln, $R_{28}$ is Ala, and $R_{36}$ is Lys.

The peptides are synthesized by a suitable method, such as by exclusively solid-phase techniques, by partial solid-phase techniques, by fragment condensation or by classical solution addition. rCRF and certain analogs which do not include D-isomer residues or unnatural amino acid residues may also be synthesized by recently developed recombinant DNA techniques.

Common to chemical synthesis of peptides is the protection of the labile side chain groups of the various amino acid moieties with suitable protecting groups which will prevent a chemical reaction from occurring at that site until the group is ultimately removed. Usually also common is the protection of an alpha-amino group on an amino acid or a fragment while that entity reacts at the carboxyl group, followed by the selective removal of the alpha-amino protecting group to allow subsequent reaction to take place at that location. Accordingly, it is common that, as a step in the synthesis, an intermediate compound is produced which includes each of the aminoacid residues located in its desired sequence in the peptide chain with various of these residues having side-chain protecting groups.

Also considered to be within the scope of the present invention are intermediates of the formula:

$X^1$-$R_1$-Pro-Pro-Ile-Ser($X^2$)-$R_8$-Asp($X^5$)-Leu-$R_{11}$($X^2$)-$R_{12}$($X^4$)-$R_{13}$(X or $X^5$)-Leu-Leu-Arg($X^3$)-$R_{17}$($X^5$ or $X^6$)-$R_{18}$-$R_{19}$($X^4$)-Glu($X^5$)-$R_{21}$-$R_{22}$($X^2$ or $X^3$)-$R_{23}$($X^3$ or $X^6$)-$R_{24}$($X^4$)-$R_{25}$($X^5$)-$R_{26}$($X^4$ or $X^6$)-$R_{27}$($X^4$ or $X^5$)-$R_{28}$($X^6$)-Gln($X^4$)-Gln($X^4$)-Ala-$R_{32}$(X)-$R_{33}$($X^2$ or $X^4$)-Asn($X^4$)-Arg($X^3$)-$R_{36}$($X^6$)-Leu-$R_{38}$-$R_{39}$($X^5$)-$R_{40}$($X^4$)-$R_{41}$($X^4$)-$X^7$ wherein: the R-groups are as hereinbefore defined.

$X^1$ is either hydrogen or an α-amino protecting group. The α-amino protecting groups contemplated by $X^1$ are those known to be useful in the art in the stepwise synthesis of polypeptides. Among the classes of α-amino protecting groups covered by $X^1$ are (1) acyl-type protecting groups, such as formyl, acrylyl(Acr), benzoyl(Bz) and acetyl(Ac) which are preferably used only at the N-terminal; (2) aromatic urethan-type protecting groups, such as benzyloxycarbonyl(Z) and substituted Z, such as p-chlorobenzyloxycarbonyl, p-nitrobenzyloxycarbonyl, p-bromobenzyloxycarbonyl, p-methoxybenzyloxycarbonyl; (3) aliphatic urethan protecting groups, such as t-butyloxycarbonyl (BOC), diisopropylmethoxycarbonyl, isopropyloxycarbonyl, ethoxycarbonyl, allyloxycarbonyl; (4) cycloalkyl urethan-type protecting groups, such as cyclopentyloxycarbonyl, adamantyloxycarbonyl, and cyclohexyloxycarbonyl; and (5) thiourethan-type protecting groups, such as phenylthiocarbonyl. The preferred α-amino protecting group is BOC.

$X^2$ is a protecting group for the hydroxyl group of Thr and Ser and is preferably selected from the class consisting of acetyl(Ac), benzoyl(Bz), tert-butyl, triphenylmethyl(trityl), tetrahydropyranyl, benzyl ether(Bzl) and 2,6-dichlorobenzyl (DCB). The most preferred protecting group is Bzl. $X^2$ can be hydrogen, which means there is no protecting group on the hydroxyl group.

$X^3$ is a protecting group for the quanidino group of Arg preferably selected from the class consisting of nitro, p-toluenesulfonyl(Tos), Z, adamantyloxycarbonyl and BOC, or is hydrogen. Tos is most preferred.

$X^4$ is hydrogen or a protecting group for the amido group of Asn or Gln and is preferably xanthyl(Xan).

$X^5$ is hydrogen or an ester-forming protecting group for the β- or γ-carboxyl group of Asp or Glu, preferably selected from the class consisting of benzyl, 2,6-dichlorobenzyl, methyl, ethyl and t-butyl ester. OBzl is most preferred.

$X^6$ is hydrogen or a protecting group for the side chain amino substituent of Lys. Illustrative of suitable side chain amino protecting groups are Z, 2-chlorobenzyloxycarbonyl(2-Cl-Z), Tos, t-amyloxycarbonyl(Aoc), BOC and aromatic or aliphatic urethan-type protecting groups as specified hereinbefore.

When His is present, X is hydrogen or a protecting group for the imidazole nitrogen such as Tos or 2,4-dinitrophenyl(DNP), and when Tyr is present, X is hydrogen or a protecting group for the hydroxyl group such as DCB. When Met is present, the sulfur may be protected, if desired, with oxygen.

The selection of a side chain amino protecting group is not critical except that it should must be one which is not removed during deprotection of the α-amino groups during the synthesis. Hence, the α-amino protecting group and the side chain amino protecting group cannot be the same.

$X^7$ is NH$_2$, a protecting group such as an ester or an anchoring bond used in solid phase synthesis for linking to a solid resin support, preferably one represented by the formulae:

—NH-benzhydrylamine (BHA) resin support and
—NH-paramethylbenzhydrylamine (MBHA) resin support. Cleavage from a BHA or MBHA resin directly gives the rCRF amide or rCRF analog amide. By employing a methyl-derivative of such a resin, a methyl-substituted amide can be created.

In the formula for the intermediate, at least one of X, $X^1$, $X^2$, $X^3$, $X^4$, $X^5$ and $X^6$ is a protecting group. The particular amino acid chosen for each the R-group determines whether there will also be a protecting group attached as specified hereinbefore and as generally known in the art. In selecting a particular side chain protecting group to be used in the synthesis of the peptides, the following rules are followed: (a) the protecting group should be stable to the reagent and under the reaction conditions selected for removing the α-amino protecting group at each step of the synthesis, (b) the protecting group should retain its protecting properties and not be split off under coupling conditions and (c) the side chain protecting group must be removable, upon the completion of the synthesis containing the desired amino acid sequence, under reaction conditions that will not alter the peptide chain.

For the acyl group at the N-terminal represented by Y, acetyl, formyl, acrylyl and benzoyl are preferred. For the 1 to 10 amino acid peptide which may be optionally included without adversely affecting the potency, any amino acids may be used, but the L- or D-forms of the naturally accurring amino acids would normally be used.

Thus, the present invention is also considered to provide a process for the manufacture of compounds defined by the formula (I): Y-$R_1$-Pro-Pro-Ile-Ser-$R_8$-Asp-Leu-$R_{11}$-$R_{12}$-$R_{13}$-Leu-Leu-Arg-$R_{17}$-$R_{18}$-$R_{19}$-Glu-$R_{21}$-$R_{22}$-$R_{23}$-$R_{24}$-$R_{25}$-$R_{26}$-$R_{27}$-$R_{28}$-Gln-Gln-Ala-$R_{32}$-$R_{33}$-Asn-Arg-$R_{36}$-Leu-$R_{38}$-$R_{39}$-$R_{40}$-$R_{41}$-$NH_2$ wherein Y is an acyl group having 7 or less carbon atoms or hydrogen; $R_1$ is Ser-Gln-Glu or pGlu-Gly or Gln-Glu or Glu or D-Ser-Gln-Glu or Ser-Glu-Glu or D-Ser-Glu-Glu or Glu-Glu or D-pGlu-Gly or des$R_1$; $R_8$, $R_{12}$, $R_{19}$, $R_{24}$ and $R_{40}$ are selected from the group consisting of Leu, Ile, Ala, Gly, Val, Nle, Phe and Gln; $R_{11}$ is Thr or Ser; $R_{13}$ is His, Tyr or Glu; $R_{17}$ is Glu or Lys; $R_{18}$ is Val or Met; $R_{21}$ is Met, Met(O), Ile, Ala, Leu, Gly, Nle, Val, Phe or Gln; $R_{22}$ is Ala or Thr or Glu; $R_{23}$ is Arg or Lys; $R_{25}$ is Asp or Glu; $R_{26}$ is Gln or Lys; $R_{27}$ is Leu, Ile, Ala, Gly, Val, Nle, Phe, Asp, Asn, Gln or Glu; $R_{28}$ is Ala or Lys; $R_{32}$ is His, Tyr or Ala; $R_{33}$ is Ser, Asn, Leu, Thr or Ala; $R_{36}$ is Lys or Leu; $R_{38}$ is Met or Leu; $R_{39}$ is Glu or Asp; $R_{41}$ is Ala, Ile, Gly, Val, Leu, Nle, Phe, Gln or des $R_{41}$, provided however that when $R_{38}$ is Leu, then $R_{22}$ is Ala; and provided further that Y may optionally include 1 to 10 amino acids; or a nontoxic addition salt thereof: comprising (a) forming a peptide having at least one protective group and having the formula II: $X^1$-$R_1$-Pro-Pro-Ile-Ser($X^2$)-$R_8$-Asp($X^5$)-Leu-$R_{11}$($X^2$)-$R_{12}$($X^4$)-$R_{13}$($X$ or $X^5$)-Leu-Leu-Arg($X^3$)-$R_{17}$($X^5$ or $X^6$)-$R_{18}$-$R_{19}$($X^4$)-Glu($X^5$)-$R_{21}$-$R_{22}$($X^2$ or $X^3$)-$R_{23}$($X^3$ or $X^6$)-$R_{24}$($X^4$)-$R_{25}$($X^5$)-$R_{26}$($X^4$ or $X^6$)-$R_{27}$($X^4$ or $X^5$)-$R_{28}$($X^6$)-Gln($X^4$)-Gln($X^4$)-Ala-$R_{32}$($X$)-$R_{33}$($X^2$ or $X^4$)-Asn($X^4$)-Arg($X^3$)-$R_{36}$($X^6$)-Leu-$R_{38}$-$R_{39}$($X^5$)-$R_{40}$($X^4$)-$R_{41}$($X^4$)-$X^7$ wherein: X, $X^1$, $X^2$, $X^3$, $X^4$, $X^5$ and $X^6$ are each either hydrogen or a protective group, and $X^7$ is either a protective group or an anchoring bond to resin support or OH or $NH_2$ and (b) splitting off the protective group or groups or anchoring bond from said peptide of the formula (II) and (c) if desired, converting a resulting peptide into a nontoxic addition salt thereof.

The peptides are preferably prepared using solid phase synthesis, such as that described by Merrifield, J. Am. Chem. Soc., 85, p 2149 (1964), although other equivalent chemical syntheses known in the art can also be used as previously mentioned. Solid-phase synthesis is commenced from the C-terminal end of the peptide by coupling a protected α-amino acid to a suitable resin as generally set forth in U.S. Pat. No. 4,244,946 issued Jan. 21, 1981 to Rivier et al., the disclosure of which is incorporated herein by reference. Such a starting material for rCRF can be prepared by attaching α-amino-protected Ile to a BHA resin.

Ile protected by BOC is coupled to the BHA resin using methylene chloride and dimethylformamide (DMF). Following the coupling of BOC-Ile to the resin support, the α-amino protecting group is removed, as by using trifluoroacetic acid(TFA) in methylene chloride, TFA alone or with HCl in dioxane. Preferably 50 volume % TFA in methylene chloride is used with 0-5 weight % 1,2 ethanedithiol. The deprotection is carried out at a temperature between about 0° C. and room temperature. Other standard cleaving reagents and conditions for removal of specific α-amino protecting groups may be used as described in Schroder & Lubke, "The Peptides", 1 pp 72-75 (Academic Press 1965).

After removal of the α-amino protecting group of Ile, the remaining α-amino- and side chain-protected amino acids are coupled step-wise in the desired order to obtain the intermediate compound defined hereinbefore. As an alternative to adding each amino acid separately in the synthesis, some of them may be coupled to one another prior to addition to the solid phase reactor. The selection of an appropriate coupling reagent is within the skill of the art. Particularly suitable as a coupling reagent is N,N'-dicyclohexyl carbodiimide(DCCI).

The activating reagents used in the solid phase synthesis of the peptides are well known in the peptide art. Examples of suitable activating reagents are carbodiimides, such as N,N'-diisopropyl carbodiimide and N-ethyl-N'-(3-dimethylaminopropyl)carbodiimide. Other activating reagents and their use in peptide coupling are described by Schroder & Lubke, supra, in Chapter III and by Kapoor, J. Phar. Sci., 59, pp 1–27 (1970).

Each protected amino acid or amino acid sequence is introduced into the solid phase reactor in about a four-fold excess, and the coupling is carried out in a medium of dimethylformamide(DMF):$CH_2Cl_2$ (1:1) or in DMF or $CH_2Cl_2$ alone. In instances where the coupling is carried out manually, the success of the coupling reaction at each stage of the synthesis is monitored by the ninhydrin reaction, as described by E. Kaiser et al., Anal. Biochem. 34, 595 (1970). In cases where incomplete coupling occurs, the coupling procedure is repeated before removal of the α-amino protecting group prior to the coupling of the next amino acid. The coupling reactions can be performed automatically, as on a Beckman 990 automatic synthesizer, using a program such as that reported in Rivier et al., Biopolymers, 1978, 17, pp. 1927–1938.

After the desired amino acid sequence has been completed, the intermediate peptide is removed from the resin support by treatment with a reagent, such as liquid hydrogen fluoride, which not only cleaves the peptide from the resin but also cleaves all remaining side chain protecting groups $X^2$, $X^3$, $X^4$, $X^5$ and $X^6$ and the α-amino protecting group $X^1$ (unless it is an acyl group which is intended to be present in the final peptide), to obtain the peptide. When using hydrogen fluoride for cleaving, anisole and methylethyl sulfide are included in the reaction vessel as scavengers. When Met is present in the sequence, the BOC protecting group may be cleaved with trifluoroacetic acid(TFA)/ethanedithiol prior to cleaving the peptide from the resin to eliminate S-alkylation.

The following Example sets forth the preferred method for synthesizing analogs of rCRF by the solid-phase technique.

EXAMPLE I

The synthesis of the rCRF having the formula: H-Ser-Glu-Glu-Pro-Pro-Ile-Ser-Leu-Asp-Leu-Thr-Phe-His-Leu-Leu-Arg-Glu-Val-Leu-Glu-Met-Ala-Arg-Ala-Glu-Gln-Leu-Ala-Gln-Gln-Ala-His-Ser-Asn-Arg-Lys-Leu-Met-Glu-Ile-Ile-$NH_2$ is conducted in a stepwise manner on a MBHA hydrochloride resin, such as available from Bachem, Inc., having a substitution range of about 0.1 to 0.5 mmoles/gm. resin. The synthesis is performed on an automatic Beckman 990B peptide synthesizer. Coupling of BOC-Ile results in the substitution of about 0.35 mmol. Ile per gram of resin. All solvents that are used are carefully degassed, preferably by sparging with an inert gas, e.g. helium or nitrogen, to insure the absence of oxygen that might undesirably oxidize the sulfur of the Met residue.

After deprotection and neutralization, the peptide chain is built step-by-step on the resin. Generally, one to two mmol. of BOC-protected amino acid in methylene chloride is used per gram of resin, plus one equivalent of 2 molar DCCI in methylene chloride, for two hours. When BOC-Arg(Tos) is being coupled, a mixture of 50% DMF and methylene chloride is used. Bzl is used as the hydroxyl side-chain protecting group for Ser and Thr. P-nitrophenyl ester(ONp) is used to activate the carboxyl end of Asn or Gln, and for example, BOC-Asn(ONp) is coupled overnight using one equivalent of HOBt in a 50% mixture of DMF and methylene chloride. The amido group of Asn or Gln is protected by Xan when DCC coupling is used instead of the active ester method. 2-Cl-Z is used as the protecting group for the Lys side chain. Tos is used to protect the guanidino group of Arg and the imidazole group of His, and the side chain carboxyl group of Glu or Asp is protected by OBzl. At the end of the synthesis, the following composition is obtained BOC-Ser(Bzl)-Glu(OBzl)-Glu(OBzl)-Pro-Pro-Ile-Ser(Bzl)-Leu-Asp(OBzl)-Leu-Thr(Bzl)-Phe-His(Tos)-Leu-Leu-Arg(Tos)-Glu(OBzl)-Val-Leu-Glu(OBzl)-Met-Ala-Arg(Tos)-Ala-Glu(OBzl)-Gln(Xan)-Leu-Ala-Gln(Xan)-Gln(Xan)-Ala-His(Tos)-Ser(Bzl)-Asn(Xan)-Arg(Tos)-Lys (2-Cl-Z)-Leu-Met-Glu(OBzl)-Ile-Ile-resin support. Xan may have been partially or totally removed by TFA treatment used to deblock the α-amino protecting group.

In order to cleave and deprotect the resulting protected peptide-resin, it is treated with 1.5 ml. anisole, 0.5 ml. of methylethylsulfide and 15 ml. hydrogen fluoride (HF) per gram of peptide-resin, first at $-20°$ C. for 20 min. and then at $0.°$ C. for one-half hour. After elimination of the HF under high vacuum, the resin-peptide is washed alternately with dry diethyl ether and chloroform, and the peptides are then extracted with degassed 2N aqueous acetic acid and separated from the resin by filtration.

The peptide is purified by gel permeation followed by semi-preparative HPLC as described in Rivier et al., *Peptides: Structure and Biological Function* (1979) pp. 125–128. The chromatographic fractions are carefully monitored by HPLC, and only the fractions showing substantial purity were pooled.

Specific optical rotation of the rCRF peptide, which was synthesized and purified in the foregoing manner, was measured on a Perkin Elmer Model 141 as $[\alpha]_D^{22°} = -93.5° \pm 1.0$ (c=1 in 1% acetic acid) (with correction for the presence of $H_2O$ and TFA) and had a purity of about 95%. To check whether the precise sequence was achieved, the rCRF peptide was hydrolyzed in sealed evacuated tubes containing constant boiling HCl, 3 μl of thioglycol/ml. and 1 nmol of Nle (as an internal standard) for 9 hours at 140° C. Amino acid analyses of the hydrolysates using a Beckman 121 MB amino acid analyzer showed the following amino acid ratios: Asp(1.9), Thr(0.8), Ser(3.1), Glu(9.0), Pro(2.1), Ala(3.8), Val(0.9), Met(1.9), Ile(2.6), Leu(7.0), Phe(0.9), Lys(1.0), His(2.0) and Arg(3.0), which confirmed that the 41-residue peptide structure had been obtained.

EXAMPLE II rCRF was extracted, isolated and purified in he following manner. Lyophilized rat hypothalami are defatted with acetone, and the resulting powder is extracted with 10 volumes of a mixture of 1N acetic acid (HOAc), 0.1N HCl, 0.5% β-mercaptoethanol, 10 mM EDTA, and 5 μg/ml pepstatin A at a temperature greater than 90° C. The hot slurry is immediately ground in a blender, cooled in an ice bath, and centrifuged. The supernatant is saved while the precipitate is re-extracted with the above mixture with the addition of 20 mM NaCl. The combined supernatants are defatted by multiple extraction with two volumes ethyl ether-petroleum ether (1:2).

The aqueous phase is subjected to gel filtration chromatography at 4° C. on a Pharmacia K 215/100 column packed with 85 cm Sephadex G-50 fine, topped with 5 cm Sephadex G-10, $V_T = 31$ liters. The eluant is 3N HOAc with 0.2% β-mercaptoethanol. Corticotropin/β-Endorphin Releasing Factor bio- and immuno-activity, along with GH releasing activity, elute in the region: $K_{av} = 0.20-0.31$. The CRF zone is further purified by preparative HPLC using Waters Associates Prep 500 system with cartridges packed with Vydac $C_{18}$ and a triethylammonium phosphate(TEAP)-/acetonitrile buffer system as described by Rivier, *J. Liquid Chromat.* 1:343–367, 1978. The active fractions are further purified by HPLC using Vydac $C_4$ semi-preparative columns and a trifluoroacetic acid/acetonitrile system.

Further purification of rCRF was carried out. First an analytical separation was carried out on Vydac diphenyl (5μ) column using TEAP/CH$_3$CN gradient. Then 2 successive analytical separations were made on Vydac $C_{18}$ (5μ) columns using 0.1% TFA/CH$_3$CN gradient. Finally 2 additional separations were made on a Vydac diphenyl (5μ) column using 0.1% TFA/CH$_3$CN gradient. The last step yielded approximately two nanomoles of (>90% pure) rCFR. Composition and structural analysis which gave the following sequence: H-Ser-Glu-Glu-Pro-Pro-Ile-Ser-Leu-Asp-Leu-Thr-Phe-His-Leu-Leu-Arg-Glu-Val-Leu-Glu-Met-Ala-Arg-Ala-Glu-Gln-Leu-Ala-Gln-Gln-Ala-His-Ser-Asn-Arg-Lys-Leu-Met-Glu-Ile-Ile-NH$_2$.

EXAMPLE III

The synthetic and the natural rCRF were examined for their effects on the secretion of ACTH and β-endorphin in vitro and the synthetic rCRF was also examined in vivo. The high potency of synthetic and natural rCRF to stimulate the secretion of ACTH and β-endorphin by cultured rat pituitary cells was measured. Minimal and half-maximal responses were observed at about 10 picomolar and about 100 picomolar of synthetic rCRF, respectively. The secretory response to maximal (>5 nM) concentrations of rCRF is at a plateau level. In vivo doses from 30 ng to 3 μg/Kg of body weight rapidly elevated ACTH and β-endorphin-like (β-END-LI) secretion 5–20 fold.

Synthetic rCRF has been shown to be a powerful stimulator of ACTH and β-END-LI secretion in vivo in several rat preparations. Plasma levels of ACTH and β-END-LI are elevated for at least 5–20 minutes following the intravenous administration of rCRF to nembutal-anesthesized male rats and to quiescent male or female rats with indwelling intravenous cannulae. In addition, rCRF is found to have a dramatic effect to lower blood pressure in rats and dogs.

EXAMPLE IV

The peptide [Acetyl-Gly$^1$]-rCRF having the formula:
Ac-Gly-Glu-Glu-Pro-Pro-Ile-Ser-Leu-Asp-Leu-Thr-Phe-His-Leu-Leu-Arg-Glu-Val-Leu-Glu-Met-Ala-Arg-Ala-Glu-Gln-Leu-Ala-Gln-Gln-Ala-His-Ser-Asn-Arg-Lys-Leu-Met-Glu-Ile-Ile-NH$_2$ is synthesized.
Testing in accordance with the general procedure set forth in Example III shows that it likewise stimulates the secretion of ACTH and β-END-LI and causes a very significant lowering of blood pressure.

EXAMPLE V

The peptide [des Ser¹-Glu²-Glu³]-rCRF having the formula:
H-Pro-Pro-Ile-Ser-Leu-Asp-Leu-Thr-Phe-His-Leu-Leu-Arg-Glu-Val-Leu-Glu-Met-Ala-Arg-Ala-Glu-Gln-Leu-Ala-Gln-Gln-Ala-His-Ser-Asn-Arg-Lys-Leu-Met-Glu-Ile-Ile-NH₂
is synthesized. Testing in accordance with the general procedure set forth in Example III shows that it likewise stimulates the secretion of ACTH and β-END-LI and causes a very significant lowering of blood pressure.

EXAMPLE VI

The peptide [Tyr-Ser¹]-rCRF having the formula:
H-Tyr-Ser-Glu-Glu-Pro-Pro-Ile-Ser-Leu-Asp-Leu-Thr-Phe-His-Leu-Leu-Arg-Glu-Val-Leu-Glu-Met-Ala-Arg-Ala-Glu-Gln-Leu-Ala-Gln-Gln-Ala-His-Ser-Asn-Arg-Lys-Leu-Met-Glu-Ile-Ile-NH₂
is synthesized. Testing in accordance with the general procedure set forth in Example III shows that it likewise stimulates the secretion of ACTH and β-END-LI and causes a very significant lowering of blood pressure.

EXAMPLE VII

The peptide [Ala¹⁹, Thr²²]-rCRF having the formula:
H-Ser-Glu-Glu-Pro-Pro-Ile-Ser-Leu-Asp-Leu-Thr-Phe-His-Leu-Leu-Arg-Glu-Val-Ala-Glu-Met-Thr-Arg-Ala-Glu-Gln-Leu-Ala-Gln-Gln-Ala-His-Ser-Asn-Arg-Lys-Leu-Met-Glu-Ile-Ile-NH₂
is synthesized. Testing in accordance with the general procedure set forth in Example III shows that it likewise stimulates the secretion of ACTH and β-END-LI and causes a very significant lowering of blood pressure.

EXAMPLE VIII

The peptide [Acrylyl-Leu-Gly-Val¹, Ser²]-rCRF having the formula:
Acr-Leu-Gly-Val-Ser-Glu-Pro-Pro-Ile-Ser-Leu-Asp-Leu-Thr-Phe-His-Leu-Leu-Arg-Glu-Val-Leu-Glu-Met-Ala-Arg-Ala-Glu-Gln-Leu-Ala-Gln-Gln-Ala-His-Ser-Asn-Arg-Lys-Leu-Met-Glu-Ile-Ile-NH₂
is synthesized. Testing in accordance with the general procedure set forth in Example III shows that it likewise stimulates the secretion of ACTH and β-END-LI and causes a very significant lowering of blood pressure.

EXAMPLE IX

The peptide [Glu¹³, Val²¹]-rCRF having the formula:
H-Ser-Glu-Glu-Pro-Pro-Ile-Ser-Leu-Asp-Leu-Thr-Phe-Glu-Leu-Leu-Arg-Glu-Val-Leu-Glu-Val-Ala-Arg-Ala-Glu-Gln-Leu-Ala-Gln-Gln-Ala-His-Ser-Asn-Arg-Lys-Leu-Met-Glu-Ile-Ile-NH₂
is synthesized. Testing in accordance with the general procedure set forth in Example III shows that it likewise stimulates the secretion of ACTH and β-END-LI and causes a very significant lowering of blood pressure to a great extent than rCRF.

EXAMPLE X

The peptide [Nle⁸, Ser¹¹, Leu³³]-rCRF having the formula:
H-Ser-Glu-Glu-Pro-Pro-Ile-Ser-Nle-Asp-Leu-Ser-Phe-His-Leu-Leu-Arg-Glu-Val-Leu-Glu-Met-Ala-Arg-Ala-Glu-Gln-Leu-Ala-Gln-Gln-Ala-His-Leu-Asn-Arg-Lys-Leu-Met-Glu-Ile-Ile-NH₂
is synthesized. Testing in accordance with the general procedure set forth in Example III shows that it likewise stimulates the secretion of ACTH and β-END-LI and causes a very significant lowering of blood pressure.

EXAMPLE XI

The peptide [Ala²¹, Leu³⁸, Nle⁴¹]-rCRF having the formula:
H-Ser-Glu-Glu-Pro-Pro-Ile-Ser-Leu-Asp-Leu-Thr-Phe-His-Leu-Leu-Arg-Glu-Val-Leu-Glu-Ala-Ala-Arg-Ala-Glu-Gln-Leu-Ala-Gln-Gln-Ala-His-Ser-Asn-Arg-Lys-Leu-Leu-Glu-Ile-Nle-NH₂
is synthesized. Testing in accordance with the general procedure set forth in Example III shows that it likewise stimulates the secretion of ACTH and β-END-LI and causes a very significant lowering of blood pressure.

EXAMPLE XII

The peptide [Benzoyl-Gly¹, des Gln³, Nle¹²]-rCRF having the formula:
Bz-Gly-Glu-Pro-Pro-Ile-Ser-Leu-Asp-Leu-Thr-Nle-His-Leu-Leu-Arg-Glu-Val-Leu-Glu-Met-Ala-Arg-Ala-Glu-Gln-Leu-Ala-Gln-Gln-Ala-His-Ser-Asn-Arg-Lys-Leu-Met-Glu-Ile-Ile-NH₂
is synthesized. Testing in accordance with the general procedure set forth in Example III shows that it likewise stimulates the secretion of ACTH and β-END-LI and causes a very significant lowering of blood pressure.

EXAMPLE XIII

The peptide [Acetyl-Pro⁴, Asp³⁹]-rCRF having the formula:
Ac-Pro-Pro-Ile-Ser-Leu-Asp-Leu-Thr-Phe-His-Leu-Leu-Arg-Glu-Val-Leu-Glu-Met-Ala-Arg-Ala-Glu-Gln-Leu-Ala-Gln-Gln-Ala-His-Ser-Asn-Arg-Lys-Leu-Met-Asp-Ile-Ile-NH₂
is synthesized. Testing in accordance with the general procedure set forth in Example III shows that it likewise stimulates the secretion of ACTH and β-END-LI and causes a very significant lowering of blood pressure to a greater extent than rCRF.

EXAMPLE XIV

The peptide [Gln², Lys²³, Leu³⁸]-rCRF having the formula:
H-Ser-Gln-Glu-Pro-Pro-Ile-Ser-Leu-Asp-Leu-Thr-Phe-His-Leu-Leu-Arg-Glu-Val-Leu-Glu-Met-Ala-Lys-Ala-Glu-Gln-Leu-Ala-Gln-Gln-Ala-His-Ser-Asn-Arg-Lys-Leu-Leu-Glu-Ile-Ile-NH₂
is synthesized. Testing in accordance with the general procedure set forth in Example III shows that it likewise stimulates the secretion of ACTH and β-END-LI and causes a very significant lowering of blood pressure.

EXAMPLE XV

The peptide [Nle$^{21}$, Tyr$^{32}$]-rCRF having the formula:
H-Ser-Glu-Glu-Pro-Pro-Ile-Ser-Leu-Asp-Leu-Thr-
Phe-His-Leu-Leu-Arg-Glu-Val-Leu-Glu-Nle-Ala-Arg-
Ala-Glu-Gln-Leu-Ala-Gln-Gln-Ala-Tyr-Ser-Asn-Arg-
Lys-Leu-Met-Glu-Ile-Ile-NH$_2$
is synthesized. Testing in accordance with the general procedure set forth in Example III shows that it likewise stimulates the secretion of ACTH and β-END-LI and causes a very significant lowering of blood pressure to a greater extent than rCRF.

EXAMPLE XVI

The peptide [des pGlu$^1$-Gly$^2$ Ala$^{21}$, Met$^{37}$]-sauvagine having the formula:
H-Pro-Pro-Ile-Ser-Ile-Asp-Leu-Ser-Leu-Glu-Leu-
Leu-Arg-Lys-Met-Ile-Glu-Ile-Ala-Lys-Gln-Glu-Lys-
Glu-Lys-Gln-Gln-Ala-Ala-Asn-Asn-Arg-Leu-Leu-
Met-Asp-Thr-Ile-NH$_2$
is synthesized. Testing in accordance with the general procedure set forth in Example III shows that it likewise stimulates the secretion of ACTH and β-END-LI and causes a very significant lowering of blood pressure.

EXAMPLE XVII

The peptide [Ala$^{21}$, Arg$^{22}$, Ile$^{39,40}$]-sauvagine having the formula:
pGlu-Gly-Pro-Pro-Ile-Ser-Ile-Asp-Leu-Ser-Leu-
Glu-Leu-Leu-Arg-Lys-Met-Ile-Glu-Ala-Arg-Lys-Gln-
Glu-Lys-Glu-Lys-Gln-Gln-Ala-Ala-Asn-Asn-Arg-
Leu-Leu-Leu-Asp-Ile-Ile-NH$_2$
is synthesized. Testing in accordance with the general procedure set forth in Example III shows that it likewise stimulates the secretion of ACTH and β-END-LI and causes a very significant lowering of blood pressure.

EXAMPLE XVIII

The peptide [Leu$^{26}$, Met$^{37}$]-sauvagine having the formula:
pGlu-Gly-Pro-Pro-Ile-Ser-Ile-Asp-Leu-Ser-Leu-
Glu-Leu-Leu-Arg-Lys-Met-Ile-Glu-Ile-Glu-Lys-Gln-
Glu-Lys-Leu-Lys-Gln-Gln-Ala-Ala-Asn-Asn-Arg-
Leu-Leu-Met-Asp-Thr-Ile-NH$_2$
is synthesized. Testing in accordance with the general procedure set forth in Example III shows that it likewise stimulates the secretion of ACTH and β-END-LI and causes a very significant lowering of blood pressure.

It is of interest that rCRF and its analogs exhibit such an extreme lowering of blood pressure. As a result, these peptides may be particularly valuable for the treatment of high blood pressure conditions and also for the treatment of patients who are to undergo certain types of surgery.

As rCRF profoundly stimulates the pituitary-adrenal-cortical axis, rCRF or its analogs should be useful to stimulate the functions of this axis in some types of patients with low endogenous glucocorticoid production. For example, rCRF should be useful in restoring pituitary-adrenal function in patients having received exogenous glucocorticoid therapy whose pituitary-adrenalcortical functions remain supressed.

Most other regulatory peptides have been found to have effects upon the central nervous system and upon the gastrointestinal tract. Because ACTH and β-END secretion is the "sine qua non" of an animal's response to stress, it was not surprising that rCRF has significant effects on the brain as a mediator of the body's stress response. Accordingly, rCRF may also find application in modifying the mood, learning and behavior of normal and mentally disordered individuals. Because rCRF and its analogs elevate the levels of ACTH, β-END, β-lipotropin, other pro-opiomelanocortin gene products and corticosterone, its administration can be used to induce their effects on the brain and its periphery to thereby influence memory, mood, pain appreciation, etc., and more specifically, alertness, depression and/or anxiety. For example, when administered into the ventricles, rCRF increases activity and improves learning performance in rats and thus may function as a natural stimulant.

rCRF and its analogs might also be of use for increasing blood flow to the gastrointestinal tract of animals, particularly humans and other animals. All CRF related peptides have been shown to dialate the mesenteric vascular bed. Also, oCRF inhibits gastric acid production, and rCRF is expected to also be effective in the treatment of gastric ulcers by reducing gastric acid production and/or inhibiting gastrointestinal functions in an animal.

rCRF, it analogs or the nontoxic addition salts thereof, combined with a pharmaceutically or veterinarily acceptable carrier to form a pharmaceutical composition, may be administered to mammals, including humans, and other animals either intravenously, subcutaneously, intramuscularly, percutaneously, e.g. intranasally, intracerebrospinally or orally. The peptides should be at least about 90% pure and preferably should have a purity of at least about 98%; however, lower purities are effective and may well be used with animals other than humans. This purity means that the intended peptide constitutes the stated weight % of all like peptides and peptide fragments present. Administration to humans may be employed by a physician to lower blood pressure or to stimulate endogenous glucocorticoid production. The required dosage will vary with the particular condition being treated, with the severity of the condition and with the duration of desired treatment.

These peptides may also be used to evaluate hypothalamic pituitary adrenal function in animals with suspected endocrine or central nervous system pathology by suitable administration followed by monitoring body functions. For example, administration may be used as a diagnostic tool to evaluate Cushing's disease and affective disorders, such as depressive illness.

Such peptides are often administered in the form of pharmaceutically or veterinarily acceptable nontoxic salts, such as acid addition salts or metal complexes, e.g., with zinc, iron, calcium, barium, magnesium, aluminum or the like (which are considered as addition salts for purposes of this application). Illustrative of such acid addition salts are hydrochloride, hydrobromide, sulphate, phosphate, tannate, oxalate, fumarate, gluconate, alginate, maleate, acetate, citrate, benzoate, succinate, malate, ascorbate, tartrate and the like. If the active ingredient is to be administered in tablet form, the tablet may contain a binder, such as tragacanth, corn starch or gelatin; a disintegrating agent, such as alginic acid; and a lubricant, such as magnesium stearate. If administration in liquid form is desired, sweetening and/or flavoring may be used, and intravenous administration in isotonic saline, phosphate buffer solutions or the like may be effected.

The peptides should be administered under the guidance of a physician, and pharmaceutical compositions will usually contain the peptide in conjunction with a conventional, pharmaceutically or veterinarily-acceptable carrier. Usually, the dosage will be from about 1 to about 200 micrograms of the peptide per kilogram of the body weight of the host animal. In some instances, treatment of subjects with these peptides can be carried out in lieu of the administration of ACTH or corticosteroids, in such instances a dosage as low as about 10 ng/Kg of body weight may be employed. As used herein all temperatures are °C. and all ratios are by volume. Percentages of liquid materials are also by volume.

Although the invention has been described with regard to its preferred embodiments, which constitute the best mode presently known to the inventors, it should be understood that various changes and modifications as would be obvious to one having the ordinary skill in this art may be made without departing from the scope of the invention which is set forth in the claims appended hereto. For example, substitutions and modifications at other positions in the rCRF peptide chain can be made in accordance with present or future developments without detracting from the potency of the analogs. For instance, instead of the simple amide at the C-terminal, a lower alkyl-substituted amide, e.g. methylamide, ethylamide, etc., may be incorporated. Likewise from one to ten additional amino acid residues can be included at the N-terminal without significantly adversely affecting biological potency. Such peptides are considered as being within the scope of the invention.

Various features of the invention are emphasized in the claims which follow.

What is claimed is:

1. A composition for lowering the blood pressure of animals comprising an effective amount of rCRF or an analog of CRF or a nontoxic addition salt thereof having a purity of at least about 5% and having the formula:

Y-$R_1$-Pro-Pro-Ile-Ser-$R_8$-Asp-Leu-$R_{11}$-R$_{12}$-$R_{13}$-Leu-Leu-Arg-$R_{17}$-$R_{18}$-$R_{19}$-Glu-$R_{21}$-$R_{22}$-$R_{23}$-$R_{24}$-$R_{25}$-$R_{26}$-$R_{27}$-$R_{28}$-Gln-Gln-Ala-$R_{32}$-$R_{33}$-Asn-Arg-$R_{36}$-Leu-$R_{38}$-$R_{39}$-$R_{40}$-$R_{41}$-NH$_2$ wherein Y is an acyl group having 7 or less carbon atoms or hydrogen; $R_1$ is Ser-Gln-Glu or pGlu-Gly or Gln-Glu or Glu or D-Ser-Gln-Glu or Ser-Glu-Glu or D-Ser-Glu-Glu or Glu-Glu or D-pGlu-Gly or des$R_1$; $R_8$, $R_{12}$, $R_{19}$, $R_{24}$ and $R_{40}$ are selected from the group consisting of Leu, Ile, Ala, Gly, Val, Nle, Phe and Gln; $R_{11}$ is Thr or Ser; $R_{13}$ is His, Tyr or Glu; $R_{17}$ is Glu or Lys; $R_{18}$ is Val or Met; $R_{21}$ is Met, Met(O), Ile, Ala, Leu, Gly, Nle, Val, Phe or Gln; $R_{22}$ is Ala or Thr or Glu; $R_{23}$ is Arg or Lys; $R_{25}$ is Asp or Glu; $R_{26}$ is Gln or Lys; $R_{27}$ is Leu, Ile, Ala, Gly, Val, Nle, Phe, Asp, Asn, Gln or Glu; $R_{28}$ is Ala or Lys; $R_{32}$ is His, Tyr or Ala; $R_{33}$ is Ser, Asn, Leu, Thr or Ala; $R_{36}$ is Lys or Leu; $R_{38}$ is Met or Leu; $R_{39}$ is Glu or Asp; $R_{41}$ is Ala, Ile, Gly, Val, Leu, Nle, Phe, Gln or des $R_{41}$, provided however that when $R_{38}$ is Leu, then $R_{22}$ is Ala; and a pharmaceutically or veterinarily acceptable liquid or solid carrier therefor.

2. A method for lowering the blood pressure and/or increasing gastrointestinal blood flow of an animal, which method comprises administering to said animal an effective amount of a composition of claim 1.

3. A method for reducing gastric acid production and/or inhibiting gastrointestinal functions in an animal which method comprises administering an effective amount of a composition of claim 1.

4. A synthetic peptide having the formula:

Y-$R_1$-Pro-Pro-Ile-Ser-$R_8$-Asp-Leu-$R_{11}$-R$_{12}$-$R_{13}$-Leu-Leu-Arg-$R_{17}$-$R_{18}$-$R_{19}$-Glu-$R_{21}$-$R_{22}$-$R_{23}$-$R_{24}$-$R_{25}$-$R_{26}$-$R_{27}$-$R_{28}$-Gln-Gln-Ala-$R_{32}$-$R_{33}$-Asn-Arg-$R_{36}$-Leu-$R_{38}$-$R_{39}$-$R_{40}$-$R_{41}$-NH$_2$ wherein Y is an acyl group having 7 or less carbon atoms or hydrogen; $R_1$ is Ser-Gln-Glu or pGlu-Gly or Gln-Glu or Glu or D-Ser-Gln-Glu or Ser-Glu-Glu or D-Ser-Glu-Glu or Glu-Glu or D-pGlu-Gly or des$R_1$; $R_8$, $R_{12}$, $R_{19}$, $R_{24}$ and $R_{40}$ are selected from the group consisting of Leu, Ile, Ala, Gly, Val, Nle, Phe and Gln; $R_{11}$ is Thr or Ser; $R_{13}$ is His, Tyr or Glu; $R_{17}$ is Glu or Lys; $R_{18}$ is Val or Met; $R_{21}$ is Met, Met(O), Ile, Ala, Leu, Gly, Nle, Val, Phe or Gln; $R_{22}$ is Ala or Thr or Glu; $R_{23}$ is Arg or Lys; $R_{25}$ is Asp or Glu; $R_{26}$ is Gln or Lys; $R_{27}$ is Leu, Ile, Ala, Gly, Val, Nle, Phe, Asp, Asn, Gln or Glu; $R_{28}$ is Ala or Lys; $R_{32}$ is His, Tyr or Ala; $R_{33}$ is Ser, Asn, Leu, Thr or Ala; $R_{36}$ is Lys or Leu; $R_{38}$ is Met or Leu; $R_{39}$ is Glu or Asp; $R_{41}$ is Ala, Ile, Gly, Val, Leu, Nle, Phe, Gln or des $R_{41}$, provided however that when $R_{38}$ is Leu, then $R_{22}$ is Ala; or a nontoxic addition salt thereof.

5. The compound of claim 4 wherein $R_{13}$ is His, $R_{17}$ is Glu, $R_{18}$ is Val, $R_{26}$ is Gln, $R_{28}$ is Ala and $R_{36}$ is Lys.

6. The compound of claim 5 wherein $R_{21}$ is Met.

7. The compound of claim 4 wherein $R_{23}$ is Arg.

8. The compound of claim 5 wherein $R_{25}$ is Glu.

9. The compound of claim 5 wherein $R_{22}$ is Ala.

10. The compound of claim 5 wherein $R_{22}$ is Ala, $R_{23}$ is Arg, $R_{25}$ is Glu, $R_{32}$ is His, $R_{33}$ is Ser, $R_{38}$ is Met and $R_{40}$ is Ile.

11. The compound of claim 5 wherein $R_{38}$ is Met.

12. The compound of claim 5 wherein $R_{39}$ is Glu.

13. The compound of claim 5 wherein $R_8$ is Leu, $R_{12}$ is Phe, $R_{19}$ is Leu, $R_{24}$ is Ala, $R_{27}$ is Leu and $R_{40}$ is Ile.

14. The compound of claim 10 wherein $R_8$ is Leu, $R_{12}$ is Phe, $R_{19}$ is Leu, $R_{24}$ is Ala, $R_{27}$ is Leu and $R_{41}$ is Ile.

15. The compound of claim 4 wherein $R_1$ is Ser-Glu-Glu and Y is Ac.

16. The compound of claim 4 wherein Y is Ac and $R_1$ is des $R_1$.

17. The compound of claim 5 wherein $R_{41}$ is des $R_{41}$.

18. The compound of claim 4 having the formula:
H-Ser-Glu-Glu-Pro-Pro-Ile-Ser-Leu-Asp-Leu-Thr-Phe-His-Leu-Leu-Arg-Glu-Val-Leu-Glu-Met-Ala-Arg-Ala-Glu-Gln-Leu-Ala-Gln-Gln-Ala-His-Ser-Asn-Arg-Lys-Leu-Met-Glu-Ile-Ile-NH$_2$.

19. A method of modulating the secretion of ACTH and corticosteroids or the secretion of β-END-LI, and other pro-opiomelanocortin gene products which comprises administering an effective amount of the compound of claim 4.

20. A method of evaluating hypothalamic pituitary adrenal function in animals with suspected endrocrine or central nervous system pathology which method comprises administering such animal an effective amount of a peptide having the formula:

Y-$R_1$-Pro-Pro-Ile-Ser-$R_8$-Asp-Leu-$R_{11}$-R$_{12}$-$R_{13}$-Leu-Leu-Arg-$R_{17}$-$R_{18}$-$R_{19}$-Glu-$R_{21}$-$R_{22}$-$R_{23}$-$R_{24}$-$R_{25}$-$R_{26}$-$R_{27}$-$R_{28}$-Gln-Gln-Ala-$R_{32}$-$R_{33}$-Asn-Arg-$R_{36}$-Leu-$R_{38}$-$R_{39}$-$R_{40}$-$R_{41}$-NH$_2$ wherein Y is an acyl group having 7 or less carbon atoms or hydrogen; $R_1$ is Ser-Gln-Glu or pGlu-Gly or Gln-Glu or Glu or D-Ser-Gln-Glu or Ser-Glu-Glu or D-Ser-Glu-Glu or Glu-Glu or D-pGlu-Gly or desR$_1$; $R_8$, $R_{12}$, $R_{19}$, $R_{24}$ and $R_{40}$ are selected from the group consisting of Leu, Ile, Ala, Gly, Val, Nle, Phe and Gln; $R_{11}$ is Thr or Ser; $R_{13}$ is His, Tyr or Glu; $R_{17}$ is Glu or Lys; $R_{18}$ is Val or Met; $R_{21}$ is Met, Met(O), Ile, Ala, Leu, Gly, Nle, Val, Phe or Gln; $R_{22}$ is Ala or Thr or Glu; $R_{23}$ is Arg or Lys; $R_{25}$ is Asp or Glu; $R_{26}$ is Gln or Lys; $R_{27}$ is Leu, Ile, Ala, Gly, Val, Nle, Phe, Asp, Asn, Gln or Glu; $R_{28}$ is Ala or Lys; $R_{32}$ is His, Tyr or Ala; $R_{33}$ is Ser, Asn, Leu, Thr or Ala; $R_{36}$ is Lys or Leu; $R_{38}$ is Met or Leu; $R_{39}$ is Glu or Asp; $R_{41}$ is Ala, Ile, Gly, Val, Leu, Nle, Phe, Gln or des $R_{41}$, provided however that when $R_{38}$ is Leu, then $R_{22}$ is Ala; or a nontoxic addition salt thereof.

* * * * *

UNITED STATES PATENT AND TRADEMARK OFFICE
CERTIFICATE OF CORRECTION

PATENT NO. : 4,489,163

DATED : December 18, 1984

INVENTOR(S) : Jean E. F. Rivier, et al.

It is certified that error appears in the above-identified patent and that said Letters Patent is hereby corrected as shown below:

Column 1, line 26, change "mets" to --met-- .

Column 7, line 60, change "he" to --the--.

Column 9, line 67, change "great" to --greater--.

Column 12, line 19, change "animals" to --mammals--.

Signed and Sealed this

Twenty-eighth Day of May 1985

[SEAL]

Attest:

DONALD J. QUIGG

Attesting Officer     Acting Commissioner of Patents and Trademarks